United States Patent [19]

Mori

[11] Patent Number: 4,900,678

[45] Date of Patent: * Feb. 13, 1990

[54] APPARATUS FOR PHOTOSYNTHESIS

[76] Inventor: Kei Mori, 3-16-3-501, Kaminoge, Setagaya-ku, Tokyo, Japan

[*] Notice: The portion of the term of this patent subsequent to Feb. 9, 2005 has been disclaimed.

[21] Appl. No.: 76,422

[22] Filed: Jul. 21, 1987

Related U.S. Application Data

[63] Continuation-in-part of Ser. No. 445,642, Nov. 30, 1982, abandoned, and Ser. No. 455,692, Jan. 5, 1983, Pat. No. 4,724,214.

[30] Foreign Application Priority Data

| Dec. 3, 1981 | [JP] | Japan | 56-194921 |
| Dec. 10, 1981 | [JP] | Japan | 56-199873 |
| Dec. 10, 1981 | [JP] | Japan | 56-199874 |
| Dec. 10, 1981 | [JP] | Japan | 56-199875 |
| Jan. 16, 1982 | [JP] | Japan | 57-005261 |
| Jul. 13, 1982 | [JP] | Japan | 57-121401 |

[51] Int. Cl.$^4$ .......... C12M 1/04; C12M 1/06; C12M 1/00; A01G 33/00

[52] U.S. Cl. .......... 435/313; 435/287; 435/315; 47/1.4

[58] Field of Search ........ 435/173, 257, 287, 289, 435/290, 313, 314, 315, 317.1, 813, 946; 422/23, 24, 186, 80, 143, 186.3; 47/1.4; 261/87, 114.4, 121.1; 250/435, 436; 350/96.15; 239/228, 237, 240

[56] References Cited

U.S. PATENT DOCUMENTS

| 1,604,739 | 10/1926 | Downs | 422/197 |
| 1,869,736 | 8/1932 | Berenbruch | 422/197 |
| 2,658,310 | 11/1953 | Cook | 435/819 X |
| 2,732,662 | 1/1956 | Myers et al. | 435/287 |
| 2,815,607 | 12/1957 | Schroeder | 435/257 X |
| 3,928,142 | 12/1975 | Smith | 435/287 |
| 3,986,297 | 10/1976 | Ichimura et al. | 47/1.4 |
| 4,173,516 | 11/1979 | Katinger et al. | 435/286 |
| 4,195,907 | 4/1980 | Zamja et al. | 350/96.15 |
| 4,389,085 | 6/1983 | Mori | 350/96.1 |
| 4,411,490 | 10/1983 | Daniel | 350/96.1 |
| 4,422,719 | 12/1983 | Orcutt | 350/96.1 X |
| 4,724,214 | 2/1988 | Mori | 435/287 |

FOREIGN PATENT DOCUMENTS

| 0081156 | 6/1983 | European Pat. Off. | 435/284 |
| 0084325 | 7/1983 | European Pat. Off. | 435/257 |
| 2502515 | 11/1975 | Fed. Rep. of Germany | 47/1.4 |
| 45-17147 | 6/1970 | Japan | 47/1.4 |
| 0086286 | 5/1982 | Japan | 435/287 |
| 00138378 | 8/1982 | Japan | 435/287 |
| 1335546 | 12/1971 | U.S.S.R. | 47/1.4 |
| 0505405 | 5/1976 | U.S.S.R. | 47/1.4 |
| 0783340 | 11/1980 | U.S.S.R. | 47/1.4 |
| 0000282 | 5/1979 | World Int. Prop. O. | 435/287 |

OTHER PUBLICATIONS

Myers, "The Growth of *Chlorella pyrenoidosa* Under Various Culture Conditions", *Plant Physiology*, vol. 19, No. 4, Oct. 1944, pp. 579–589.

*Primary Examiner*—Randall E. Deck
*Attorney, Agent, or Firm*—Jordan and Hamburg

[57] ABSTRACT

An apparatus for photosynthesis has a reaction bath in which a plurality of narrow tubular photoradiators are arranged to radiate light therefrom and spaced from each other by a distance which is not more than about 2 mm. Each photoradiator has a cross-section which is cylindrical, equilateral triangular, tetragonal or hexagonal. A baffle plate is disposed below the photoradiators and is formed with a number of apertures therethrough in a predetermined area thereof which may be a radially central area or a generally annular peripheral area. $CO_2$-containing air is fed into the reaction bath through the apertures in the baffle plate to circulate along a predetermined path inside the reaction bath due to the remaining non-apertured part of the baffle plate. The function of the baffle plate may be performed by plugging which blocks the passage of the air through the spacings between the lower ends of the adjacent photoradiators in the predetermined area. The circulation of the air may be caused more positively along a variable path by a rotor which is positioned below the photoradiators and rotatable by ejecting the air while supplying it to the interior of the reaction bath. The rotor is cushioned and supported by the air ejected therefrom during operation.

3 Claims, 9 Drawing Sheets

APPARATUS FOR PHOTOSYNTHESIS

This is a Continuation-in-Part application of U.S. patent application Ser. No. 445,642 filed Nov. 30, 1982 now abandoned, and U.S. Ser. No. 455,692 filed Jan. 5, 1983 (now U.S. Pat. No. 4,724,214, issued Feb. 9, 1988).

BACKGROUND OF THE INVENTION

The present invention relates to an apparatus for effectively photosynthesizing photosynthetic substances such as algae typified by chlorella or spirolina, photosynthetic bacteria or artificial photosynthetic substances such as callus.

Photosynthetic apparatuses heretofore proposed include an apparatus for culturing chlorella (unicellular microorganism containing chlorophyl). Difficulty experienced in culturing chlorella is that illumination with intensities higher than a certain level destructs the chlorophyl and produces a toxin (phaeophorbite) while illumination with intensities lower than a certain level fails to cause photosynthesis altogether. It is therefore a primary requisite for effective photosynthesis that all the cells containing photosynthetic substances be supplied with constant light of an even distribution. Generally, organisms in a swarm increase not only their multiplying ability per unit volume but their resistance to other funge. The culturing efficiency, therefore, grows poor unless a predetermined light radiating area per one liter of culture medium is ensured. With this in view, it has been customary to promote the transmission of light by reducing the number of photosynthetic substances (individuals). This involves an inconsistency, however, because an increase in the number of individuals lowers the transmissibility to light and, therefore, requires collection of the individuals, but the resulting decrease in the number of individuals weakens the resistance to the funge. Another drawback hitherto encountered is that the light intensity is excessively high for the individuals near a light source but is insufficient for those remote from the light source and, additionally, the light is absorbed by water to have its wavelength component varied. An ideal situation is, therefore, that photosynthetic substances be passed through a very narrow clearance while a predetermined intensity of light is directed perpendicular to the clearance. Then, sufficient light will be evenly applied to all the cells containing photosynthetic substances with a minimum of attenuation and without any change in its wavelength component. A photosynthetic apparatus presently in use includes a number of fluorescent lamps arranged in a reaction bath (e.g. chlorella culturing bath) and causes photosynthetic substances to flow through the gaps between the lamps. However, the use of fluorescent lamps renders the apparatus bulky, increases power consumption and requires an awkward measure against heat generation by the lamps. Moreover, fluorescent lamps generally have peaks at specific wavelengths and those having a peak in their green component, which is harmful for chlorophyl, are unsuitable for photosynthesis. Apparently, sunlight or like natural light is most adequate for culturing chlorella and the like.

While the even supply of a sufficient amount of carbon dioxide ($CO_2$) all over the reaction bath is essential in attempting efficient photosynthesis, it has been quite difficult so far to fulfill such a condition.

Additionally, no effective means has been proposed for preventing contamination by the dead part of a photosynthetic substance or the like which tends to accumulate in various sections of a reaction bath.

In culturing chlorella, for example, one liter of culture medium extends over an area of 1 $m^2$ when spread to a thickness of 1 mm. Meanwhile, when the culture medium is laid on a 1 $m^2$ plane light source to a thickness of 1 mm, the intensity of the light source being assumed to be 1000 lx, the intensity after the light has passed through the 1 mm thick culture medium is reduced to about 30 lx in the case of a high density chlorella culture medium for enhancing the multiplying ability. Thus, hardly any light is allowed to reach chlorella located opposite to the plane light source. Although such a problem may be solved if plane light sources are located at both sides of the 1 mm thick culture medium, such results in generation of a significant amount of heat when the light sources comprise fluorescent lamps, as has been the case with conventional apparatuses.

Air is blown into the chlorella culturing bath from below in order to cause upwardly directed bubbling within the bath. Carbon dioxide ($CO_2$) contained in the air which is the source of bubbling contributes to photosynthesis of chlorella, while oxygen ($O_2$) resulting from the photosynthesis is discharged from the top of the bath. This promotes effective photosynthesis of chlorella.

The bubbling also serves to effectively diffuse and transmit light which is radiated by the photoradiators, and to agitate the cells from distributing the light to all the cells in the bath.

Furthermore, the bubbling keeps the surfaces of the photoradiators clear by exchanging gas, i.e. charging $CO_2$ and discharging $O_2$, preventing chlorella from being precipitated in a lower portion of the bath, and removing cells which deposit on the surfaces of the photoradiators. Thus it is a precondition in practicing the present invention that the apparatus be used in a vertical or upright position; using it in a horizontal position would not allow the bubbling to flow smoothly.

In accordance with the present invention, the distance between the photoradiators is selected to cope with the fact that mucilage coming out from the chlorella cells develops bubbles and these bubbles combine to form larger bubbles which tend to block the flow of the bubbling.

As described above, the present invention provides a chlorella culturing apparatus which uses bubbling. Another characteristic feature of the present invention is the instrumentation for solving problems which stem from generation of heat: that is, a light source is implemented by light which is guided by optical fibers, and light from the light source is distributed in an even intensity and an optimum quantity to all the cells in the bath. In detail, where 1 liter of culture fluid is poured onto a surface of 1 $mm^2$, it spreads to a depth of 1 mm. When light with a luminous intensity of 1,000 lx is projected onto the 1 mm deep culture fluid, the intensity is reduced to as low as 30 lx after the transmission of the light through the fluid; photosynthesis is almost impossible at such a low intensity. Fluorescent lamps used to implement a 1,000 lx planar light source would generate excessive heat to obstruct effective chlorella culturing and, in addition, bring about the need for a special device for removing the heat, thereby increasing the cost and size of the apparatus. Bubbling in accordance with the present invention enhances diffusion and transmission of light through the culture fluid so that sufficient light is supplied to the whole chlorella to promote effective chlorella culturing.

Another advantage of the present invention is that since the photoradiators are individually provided with a triangular, rectangular, hexagonal, circular and other cross-sections, they can always be held in the same relationship, enabling the apparatus to be scaled up or down with ease.

An apparatus for photosynthesis embodying the present invention includes a photosynthetic reaction bath and a plurality of tubular photoradiators arranged upright in the reaction bath in parallel with each other. The reaction bath is communicated to a source of $CO_2$-containing air supply. A circulation means is provided for circulating in the reaction bath the $CO_2$-containing air which is fed from the conduit into the reaction bath.

In accordance with the present invention, a photosynthetic reaction bath has thereinside a number of photoradiators in the form of narrow upright tubes. A baffle plate is disposed below the photoradiators and is formed with a number of apertures therethrough in a predetermined area thereof which may be a radially central area or a generally annular peripheral area. $CO_2$-containing air is fed into the reaction bath through the apertures in the baffle plate to circulate along a predetermined path inside the reaction bath due to the remaining non-apertured part of the baffle plate. The function of the baffle plate may be performed by plugging which blocks the passage of the air through the spacings between the lower ends of the adjacent photoradiators in the predetermined area. The circulation of the air may be caused more positively along a variable path by a rotor which is positioned below the photoradiators and rotatable by ejecting the air while supplying it to the interior of the reaction bath. The rotor is cushioned and rotatably supported by the air ejected therefrom during operation.

SUMMARY OF THE INVENTION

An apparatus for photosynthesis embodying the present invention comprises a photosynthetic reaction bath. A plurality of photoradiators are arranged in the reaction bath to radiate light and each of these photoradiators has a narrow tubular configuration and is spaced from the adjacent photoradiators by a distance which is not more than about 2 mm, with each of the photoradiators radiating light therefrom in an even intensity distribution.

In accordance with the present invention, an apparatus for photosynthesis has a reaction bath in which a plurality of narrow tubular photoradiators are arranged to radiate light and spaced from each other by a distance which is not more than about 2 mm. Each photoradiator has a cross-section which is cylindrical, equilateral triangular, tetragonal or hexagonal.

It is an object of the present invention to provide a new apparatus for photosynthesis which effectively promotes photosynthesis.

It is another object of the present invention to provide an apparatus for photosynthesis which eliminates the need for a measure against heat generation by a light source.

It is another object of the present invention to provide an apparatus for photosynthesis which can be readily scaled up as desired.

It is another object of the present invention to provide a generally improved apparatus for photosynthesis.

It is another object of the present invention to provide an apparatus for photosynthesis which sets up an even distribution of $CO_2$-containing air for all the cells in a reaction bath.

It is another object of the present invention to provide an apparatus for photosynthesis which automatically keeps its interior clean for a long period of time to facilitate services.

Other objects, together with the foregoing, are attained in the embodiments described in the following description and illustrated in the accompanying drawings.

DESCRIPTION OF THE PREFERRED EMBODIMENTS

While the apparatus for photosynthesis of the present invention is susceptible of numerous physical embodiments, depending upon the environment and requirements of use, substantial numbers of the herein shown and described embodiments have been made, tested and used, and all have performed in an eminently satisfactory manner.

Figure 1:
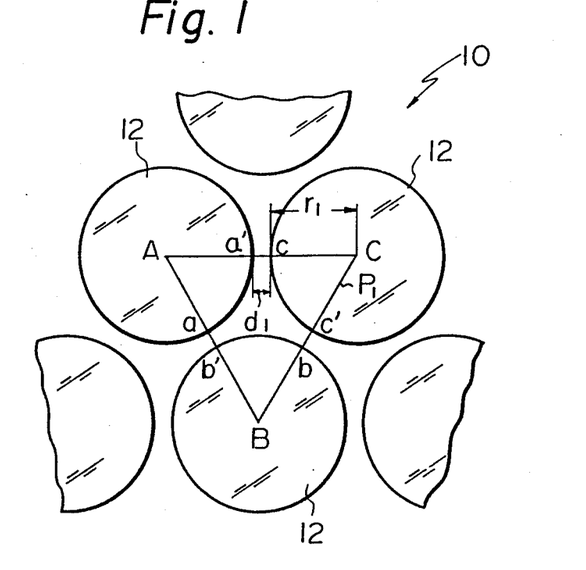
FIG. 1 is a fragmentary enlarged horizontal cross-section of a photosynthetic apparatus embodying the present invention.

Referring to FIG. 1 of the drawings, a photosynthetic reaction bath in accordance with the present invention is shown and generally designated by the reference numeral 10. A number of photoradiators 12 are disposed in the reaction bath 10 at regular spacings $d_1$. Each photoradiator 12 has a radius of $r_1$ cm.

Suppose that arbitrarily selected adjacent three of the photoradiators 12 have centers A, B and C as illustrated. Then, the triangle $P_1$(ABC) has an area $S_1$ which is expressed as:

$$S_1 = (2r_1 + d_1)^2 \cos 30° \times \frac{1}{2} \quad \text{Eq. (1)}$$

The sectors $Aaa' + Bbb' + Ccc'$ have an area $S_2$ which is given by:

$$S_2 = \left(\pi r_1^2 \times \frac{1}{6}\right) \times 3 = \pi r_1^2 \times \frac{1}{2} \quad \text{Eq. (2)}$$

The area $S_3$ defined by $ab'bc'ca'$ is obtained as:

$$S_3 = S_1 - S_2 = \frac{1}{2}\{(2r_1 + d_1)^2 \cos 30° - \pi r_1^2\} \quad \text{Eq. (3)}$$

Further, the arcs $aa' + bb' + cc'$ have a total length g which is:

$$g = 2\pi r_1 \times \frac{3}{6} \quad \text{Eq. (4)}$$

Assuming that each photoradiator 12 has a length $H_1$ (see FIG. 2), then the volume of culture medium $W_1$ allowed to flow through the area $S_3$ is expressed as:

$$W_1 = H_1 \times S_3 = \frac{H_1}{2}\{(2r_1 + d_1)^2 \cos 30° - \pi r_1^2\} \quad \text{Eq. (5)}$$

The above-mentioned amount of culture medium $W_1$ contacts the photoradiators 12 over an area S which is:

$$S = H_1 \times g = H_1 \pi r_1 \quad \text{Eq. (6)}$$

Hence, the contact area per unit culture medium, $S/W_1$, is given by:

$$S/W_1 = \frac{2\pi r_1}{(2r_1 + d_1)^2 \cos 30° - \pi r_1^2} \quad \text{Eq. (7)}$$

$$= \frac{H_1 \pi r_1}{\frac{H_1}{2}\{(2r_1 + d_1)^2 \cos 30° - \pi r_1^2\}}$$

With respect to various values of the radius $r_1$ of the photoradiators 12 and distance $d_1$ between the adjacent photoradiators 12, the factors S, $W_1$ and $S/W_1$ were obtained as indicated in Table 1 shown below.

TABLE 1

| cm $d_1$ | cm $r_1$ | cm $H_1$ | cm² S | cm³ $W_1$ | m²/l $S/W_1$ |
|---|---|---|---|---|---|
| 0 | 0.5 | 30 | 47.12 | 1.209 | *3.896 |
|  | 1.0 | 30 | 94.25 | 4.838 | *1.948 |
|  | 2.0 | 30 | 188.50 | 19.351 | 0.974 |
| 0.05 | 0.5 | 30 | 47.12 | 2.541 | *1.855 |
|  | 1.0 | 30 | 94.25 | 7.468 | *1.262 |
|  | 2.0 | 30 | 188.50 | 24.58 | 0.767 |
| 0.1 | 0.5 | 30 | 47.12 | 3.937 | #1.1969 |
|  | 1.0 | 30 | 94.25 | 10.16 | 0.9273 |
|  | 2.0 | 30 | 188.50 | 29.87 | 0.6310 |
| 0.2 | 0.5 | 30 | 47.12 | 6.925 | 0.6805 |
|  | 1.0 | 30 | 94.25 | 15.75 | 0.5984 |

TABLE 1-continued

| cm $d_1$ | cm $r_1$ | cm $H_1$ | cm² S | cm³ $W_1$ | m²/l $S/W_1$ |
|---|---|---|---|---|---|
|  | 2.0 | 30 | 188.50 | 40.65 | 0.464 |
| 0.3 | 0.5 | 30 | 47.12 | 10.17 | 0.4633 |
|  | 1.0 | 30 | 94.25 | 21.60 | 0.4364 |
|  | 2.0 | 30 | 188.50 | 51.70 | 0.3646 |

It will be seen from Table 1 that the condition $m^2/l \geq 1$ previously discussed is satisfied by five different ratios $S/W_1$ as indicated by marks "*" and "#". However, the spacing $d_1$ which is zero is impractical because it allows no culture medium to be recirculated, while 0.5 mm of spacing $d_1$ is difficult to be accurately defined during manufacture. Thus, a ratio $S/W_1$ which can be put to practical use is the one marked "#" in Table 1 provided by the spacing $d_1$ of 1 mm and the diameter of 10 mm. Concerning the spacing $d_1$, it will be noted that about 1.2 mm at the maximum is allowable in view of the fact that bubbling is usually caused by carbon dioxide in the culture medium. To promote continuous operation, the reaction bath 10 may be provided with a hermetically sealed structure which avoids contamination to the culture medium, evaporation of water, etc. The number of photoradiators 12 can readily be increased while satisfying the condition $m^2/l \geq 1$, promoting the ease of scale-up of the apparatus. For the triangular photoradiators 12, the reaction bath may have a triangular, square, hexagonal or circular cross-section.

Figure 2:
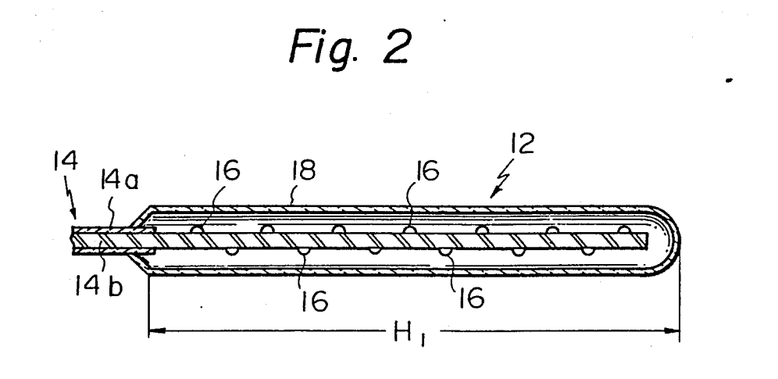
FIG. 2 is a view of a photoradiator applicable to the apparatus shown in FIG. 1.

Referring to FIG. 2, a preferred example of the photoradiators 12 applicable to the apparatus shown in FIG. 1 is illustrated. The photoradiator 12 includes a light transmitting cable generally designated by the reference numeral 14. The cable 14 comprises a clad layer 14a, a core 14b, and a number of light diffusing members 16 each adhered to the core 14b. The assembly is hermetically encapsulated in a transparent casing 18. The solar rays are collected by an apparatus, not shown, and conducted through the cable 14. The light rays reached the interior of the casing 18 are diffused by the diffusers 16 to the outside (into the reaction bath 10) via the transparent casing 18. In the illustrated embodiment, such photoradiators 12 are arranged regularly in the reaction bath 10 so as to achieve the operation and effect previously discussed.

Figure 3:
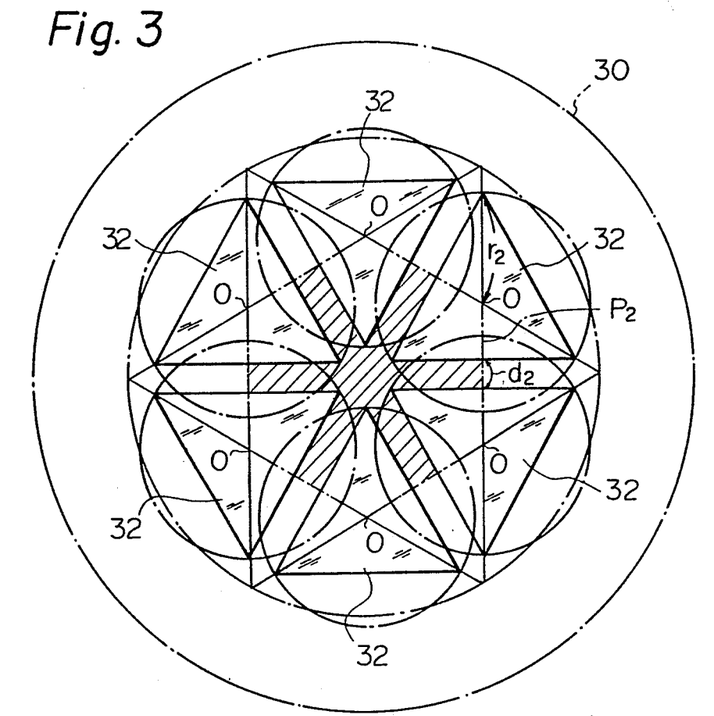
FIG. 3 is a fragmentary enlarged horizontal cross-section of another embodiment of the present invention.

Referring to FIG. 3, another embodiment of the photosynthetic apparatus of the present invention is shown. The apparatus comprises a photosynthetic reaction bath 30 in which a number of photoradiators 32 are arranged in neat order at a common spacing $d_2$. Each photoradiator 32 has an equilateral triangular cross-section and a radius of $r_2$ cm (one side being dimensioned $r_2 \times \cos 30°$).

As in the first embodiment, arbitrarily selected adjacent six of the photoradiators 32 are assumed to have centers O which define a hexagon $P_2$. Then, the total area (hatched in FIG. 3) $S_4$ of the spacings or gaps within the hexagon $P_2$ is expressed as:

$$S_4 = 6 d_2 r_2 \cos 30° + 3 d_2^2 \cos 30° \quad \text{Eq. (8)}$$

$$= 3 d_2 \cos 30° (2r_2 + d_2)$$

Supposing that the length $H_2$ of each photoradiator 32 is 30 cm, the volume $W_2$ of the culture medium allowed into the total gap is given by:

$$W_2 = H_2 \times S_4 \qquad \text{Eq. (9)}$$
$$= 30 \times 3\, d_2 \cos 30° \,(2r_2 + d_2)$$
$$= 90 \times d_2 \cos 30° \,(2r_2 + d_2)$$

Meanwhile, the photoradiators 32 contact the culture medium over an area S which is:

$$S^R = H_2 \times 12 \times r_2 \cos 30° = 360\, r_2 \cos 30° \qquad \text{Eq. (10)}$$

The various values indicated in Table 2 were obtained with respect to parameters which were the radius $r_2$ of each photoradiator 32 and the distance $d_2$ between the adjacent photoradiators 32.

TABLE 2

| $d_2$ cm | $r_2$ cm | $H_2$ cm | S' cm² | $W_2$ cm³ | S'/$W_2$ m²/l |
|---|---|---|---|---|---|
| 0.05 | 0.5 | 30 | 155.88 | 4.092 | 3.809 |
|  | 1.0 | 30 | 311.77 | 7.989 | 3.902 |
|  | 2.0 | 30 | 623.54 | 15.78 | 3.951 |
| 0.1 | 0.5 | 30 | 155.88 | 8.574 | 1.818 |
|  | 1.0 | 30 | 311.77 | 16.37 | 1.905 |
|  | 2.0 | 30 | 623.54 | 31.96 | 1.951 |
| 0.17 | 0.5 | 30 | 155.88 | 15.50 | 1.005 |
|  | 1.0 | 30 | 311.77 | 28.75 | 1.084 |
|  | 2.0 | 30 | 623.54 | 55.25 | 1.128 |
| 0.18 | 0.5 | 30 | 155.88 | 16.55 | 0.942 |
|  | 1.0 | 30 | 311.77 | 30.58 | 1.019 |
|  | 2.0 | 30 | 623.54 | 56.64 | 1.013 |
| 0.2 | 0.5 | 30 | 155.88 | 18.71 | 0.833 |
|  | 1.0 | 30 | 311.77 | 34.29 | 0.909 |
|  | 2.0 | 30 | 623.54 | 65.47 | 0.952 |
| 0.3 | 0.5 | 30 | 155.88 | 30.39 | 0.513 |
|  | 1.0 | 30 | 311.77 | 53.78 | 0.579 |
|  | 2.0 | 30 | 623.54 | 100.54 | 0.620 |

As shown in Table 2, the ratio S'/$W_2$ satisfies the condition $m^2/l \geq 1$ as long as the distance $d_2$ between the adjacent photoradiators 32 is not more than about 0.18 cm. It will be seen from Table 2 that the ratio S'/$W_2$ substantially depends upon the distance $d_2$ and is hardly effected by the diameter ($r_2$) of the photoradiators. Again, the culture medium is usually caused to bubble by carbon dioxide and this permits the distance $d_2$ to become somewhat longer than the upper-limit mentioned, i.e. up to about 2 mm in practice. Air is blown in to the chlorella culturing bath from below in order to cause upwardly directed bubbling within the bath. Carbon dioxide ($C)_2$) contained in the air which is the source of bubbling contributes to photosynthesis of chlorella, while oxygen ($O_2$) resulting from the photosynthesis is discharged from the top of the bath. Such promotes effective photosynthesis of chlorella. The bubbling also serves to effectively diffuse and transmit light which is radiated by the photoradiators, and to agitate the cells for distributing the light to all the cells in the bath.

Thus, in this embodiment, pnotosynthesis can effectively occur without being effected by the size of the photoradiators 32 only if the gap $d_2$ between the photoradiators 32 is maintained not more than about 2 mm. It is possible, therefore, to use photoradiators of various sizes in combination. For example, some of the photoradiators 32 may comprise fluorescent lamps to emit artificial light while the rest may comprise photoradiators of a relatively small diameter, compared to the photoradiators associated with the fluorescent lamps, to emit natural light from optical fibers. With this combination, photosynthesis will occur during daytime taking advantage of the sunlight and, during nighttime or the like, aided by the fluorescent lamps. Furthermore, because the photoradiators using optical fibers are capable of guiding sunlight (natural light) or artificial light emitted from a fluorescent lamp or xenon lamp as desired, various combinations of sunlight and artificial light are available such as introducing sunlight during daytime and artificial light during nighttime or introducing sunlight into a predetermined number of the photoradiators and artificial light into the rest. Due to the triangular cross-section, the photoradiators 32 can be arranged effectively in the reaction bath 29 if the reaction bath is provided with a triangular, square or hexagonal contour. Again, the reaction bath 29 can operate continuously without contamination to the culture medium or evaporation of water if provided with a hermetically sealed structure. The number of the photoradiators 32 can be readily increased under the condition concerned, i.e., $m^2/l \geq 1$, facilitating the scale-up of the apparatus.

The bubbling keeps the surfaces of the photoradiators clear by exchanging gas, i.e. charging $CO_2$ and discharging $O_2$, preventing chlorella from being precipitated in a lower portion of the bath, and removing cells which deposit on the surfaces of the photoradiators. Thus it is a precondition in practicing the present invention that the apparatus be used in a vertical or upright position; using it in a horizontal position would not allow the bubbling to flow smoothly.

In accordance with the present invention, the distance between the photoradiators is selected to cope with the fact that mucilage coming out from the chlorella cells develops bubbles and these bubbles combine to form larger bubbles which tend to block the flow of the bubbling.

As described above, applicant's invention provides a chlorella culturing apparatus which uses bubbling. Another characteristic feature of the present invention is the instrumentation for solving problems which stem from generation of heat, that is, a light source is implemented by light which is guided by optical fibers, and light from the light source is distributed in an even intensity and an optimum quantity to all the cells in the bath. In detail, where 1 liter of culture fluid is poured onto a surface of 1 mm², it spreads to a depth of 1 mm. When light with a luminous intensity of 1,000 lx is projected onto the 1 mm deep culture fluid, the intensity is reduced to as low as 30 lx after the transmission of the light through the fluid; photosynthesis is almost impossible at such a low intensity. Fluorescent lamps used to implement a 1,000 lx planar light source would generate excessive heat to obstruct effective chlorella culturing and, in addition, bring about the need for a special device for removing the heat, thereby increasing the cost and size of the apparatus. Bubbling in accordance with the present invention enhances diffusion and transmission of light through the culture fluid so that sufficient light is supplied to the whole chlorella to promote effective chlorella culturing.

Another advantage of the present invention is that since the photoradiators are individually provided with a triangular, rectangular, hexagonal, circular and other cross-sections, they can always be held in the same relationship, enabling the apparatus to be scaled up or down with ease.

Figure 4:
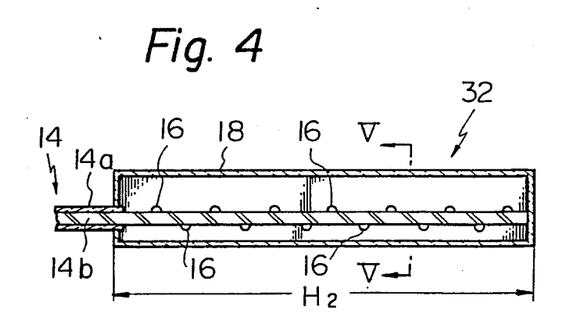
FIG. 4 is a view of a photoradiator applicable to the apparatus shown in FIG. 3.
Figure 5:
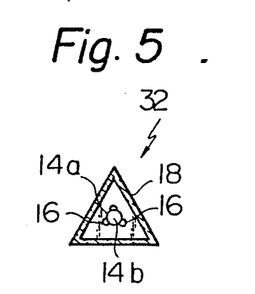
FIG. 5 is a section along line V—V of FIG. 4.

FIGS. 4 and 5 illustrate an example of the photoradiators 32 which is suitable for emitting natural light for photosynthesis. In these drawings, the same elements as those shown in FIG. 2 are designated by like reference numerals.

Figure 6:
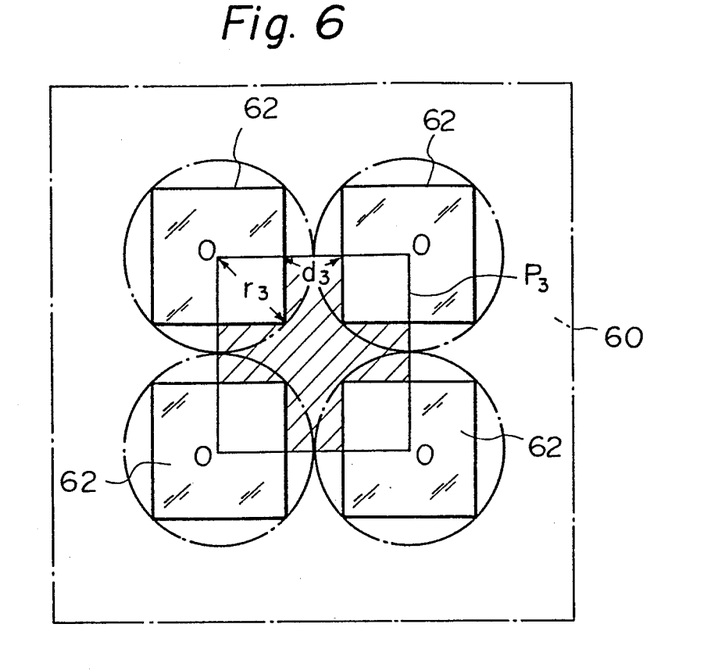
FIG. 6 is a fragmentary enlarged horizontal cross-section of another embodiment of the present invention.

Referring to FIG. 6, another embodiment of the present invention is shown which comprises a photosynthetic reaction bath 60. A number of photoradiators are arranged in the reaction bath 60 at regular spacings of $d_3$. Each photoradiator 62 has a square cross-section with a radius of $r_3$ cm (one side being dimensioned $r_3 \times \cos 45°$).

Let it be supposed that arbitrarily selected four adjacent photoradiators 62 have centers O which define a square $P_3$. Then, the total area (hatched in FIG. 6) $S_5$ of the gaps between the photoradiators 62 within the square $P_3$ is expressed as:

$$S_5 = r_3 \cos 45° \times d_3 \times 4 + d_3^2 \qquad \text{Eq. (11)}$$
$$= d_3(d_3 + 4r_3 \cos 45°)$$

Where the length $H_3$ of the photoradiators 62 is 30 cm for example, the volume $W_3$ of the culture medium which the gaps can accommodate is given by:

$$W_3 = H_2 \times S_5 \qquad \text{Eq. (12)}$$
$$= H_3 d_3 (d_3 + 4r_3 \cos 45°)$$

Meanwhile, the area $S''$ over which the light emitting surfaces of the photoradiators 62 contact the culture medium is obtained as:

$$S'' = 2r_3 \cos 45° \times 4 \times H_3 \qquad \text{Eq. (13)}$$
$$= (8r_3 \cos 45°) \times H_3$$

The factors $S''$, $W_3$ and $S''/W_3$ obtained with respect to various values of the radius $r_3$ of the phbtoradiators 62 and their gaps $d_3$ are indicated in Table 3.

TABLE 3

| cm $d_3$ | cm $r_3$ | cm $H_3$ | cm$^2$ $S''$ | cm$^3$ $W_3$ | m$^2$/l $S''/W_3$ |
|---|---|---|---|---|---|
| 0.05 | 0.5 | 30 | 84.85 | 2.1961 | 3.861 |
|  | 1.0 | 30 | 169.7 | 4.3176 | 3.930 |
|  | 2.0 | 30 | 339.41 | 8.563 | 3.965 |
|  | 3.0 | 30 | 509.1 | 12.803 | 3.976 |
| 0.1 | 0.5 | 30 | 84.85 | 4.543 | 1.868 |
|  | 1.0 | 30 | 169.7 | 8.785 | 1.932 |
|  | 2.0 | 30 | 339.41 | 17.27 | 1.965 |
|  | 3.0 | 30 | 509.1 | 25.76 | 1.977 |
| 0.17 | 0.5 | 30 | 84.85 | 8.078 | 1.050 |
|  | 1.0 | 30 | 169.7 | 15.289 | 1.109 |
|  | 2.0 | 30 | 339.41 | 29.712 | 1.142 |
|  | 3.0 | 30 | 509.1 | 44.135 | 1.153 |
| 0.18 | 0.5 | 30 | 84.85 | 8.607 | 0.986 |
|  | 1.0 | 30 | 169.7 | 16.243 | 1.045 |
|  | 2.0 | 30 | 339.41 | 31.51 | 1.077 |
|  | 3.0 | 30 | 509.1 | 46.78 | 1.088 |
| 0.2 | 0.5 | 30 | 84.85 | 9.685 | 0.8761 |
|  | 1.0 | 30 | 169.7 | 18.171 | 0.9339 |
|  | 2.0 | 30 | 339.41 | 35.141 | 0.9658 |
|  | 3.0 | 30 | 509.1 | 52.112 | 0.9769 |
| 0.3 | 0.5 | 30 | 84.85 | 15.43 | 0.5499 |
|  | 1.0 | 30 | 169.7 | 28.16 | 0.6027 |
|  | 2.0 | 30 | 339.41 | 53.61 | 0.633 |

As shown in Table 3, the ratio $S''/W_3$ satisfies the condition $m^2 \geq 1$ as long as the distance $d_3$ between the adjacent photoradiators 62 is not more than about 0.18 cm. It will be seen from Table 2 that the ratio $S''/W_3$ substantially depends upon the distance $d_3$ and is hardly effected by the diameter ($r_3$) of the photoradiators 62.

Again, the culture medium is usually caused to bubble by carbon dioxide and this permits the distance $d_2$ to become somewhat larger than the upper limit mentioned, i.e. up to about 2 mm in practice. For the square photoradiators 62, the reaction bath may have a square or circular cross-section.

Figures 7, 8:
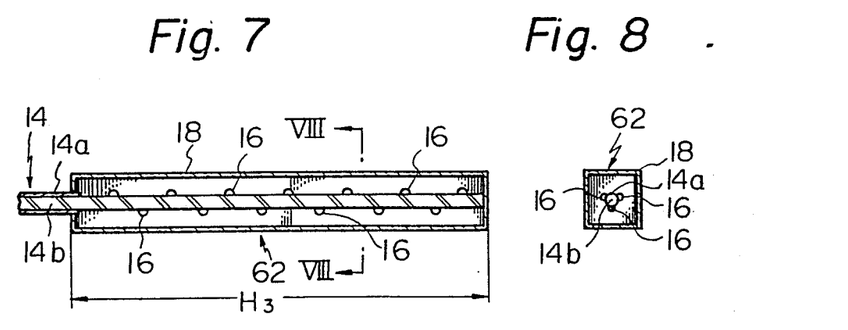
FIG. 7 is a view of a photoradiator applicable to the apparatus shown in FIG. 6.
FIG. 8 is a section along line VIII—VIII of FIG. 7.

FIGS. 7 and 8 illustrate an example of the photoradiators 62 which is suitable for guiding and emitting natural light in connection with the embodiment shown in FIG. 6. In these drawings, the same elements as those shown in FIG. 2 are designated by the same reference numerals.

Figure 9:
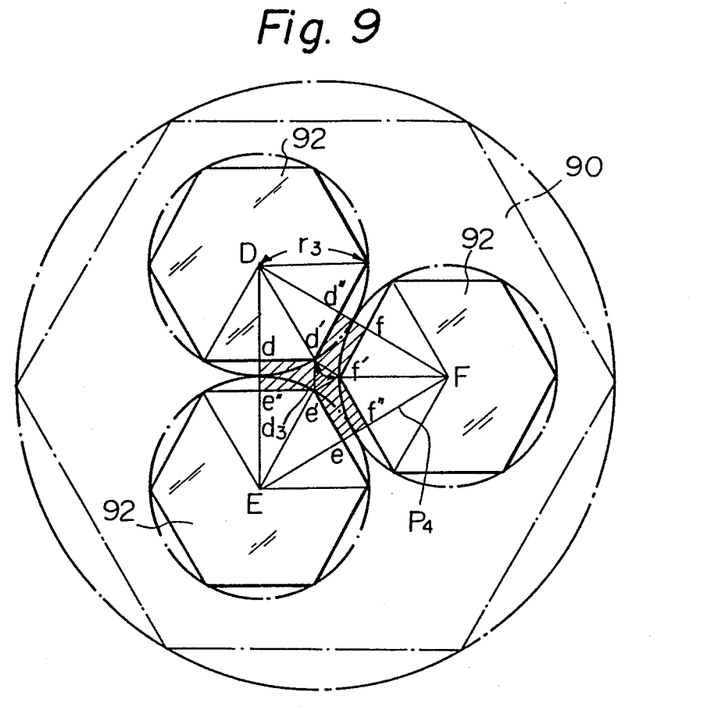
FIG. 9 is a fragmentary enlarged horizontal cross-section of still another embodiment of the present invention.
Figure 10:
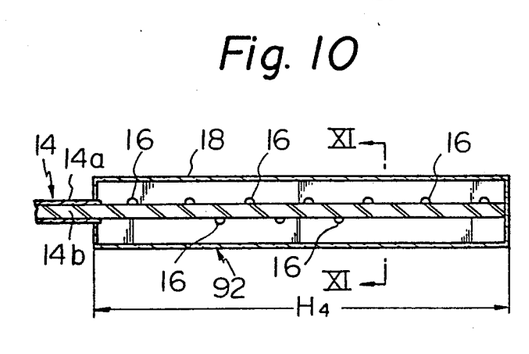
FIG. 10 is a view of a photoradiator applicable to the apparatus shown in FIG. 9.

Referring to FIG. 9, still another embodiment of the present invention is shown which comprises a photosynthetic reaction bath 90. Arranged regularly inside the reaction bath 90 are a number of photoradiators 92. Each of these photoradiators 92 has a hexagonal cross-section one side (radius) of which is $r_3$ cm long and is spaced $d_3$ from the adjacent photoradiators 92.

As in the foregoing embodiments, arbitrarily selected three of the photoradiators 92 have centers D, E and F, respectively. Lines DE, EF and FA interconnecting the centers D, E and F are assumed to intersect the light radiating surfaces of the photoradiators 92 at points d, e'', e, f'', f and d''. Further, the segments bisecting the interior angles of the triangle $P_4$ (DEF) are assumed to intersect the light emitting surfaces of the photoradiators 92 at points d', e' and f'. Then, the area $S_6$ of the triangle d'f'e' is expressed as:

$$S_6 = d_4^2 \cos 30° \times \frac{1}{2} \qquad \text{Eq. (14)}$$

The area $S_7$ of the tetragons dd'e'e''+ee'ff''+ff'd'd'' is given by:

$$S_7 = \frac{1}{2} r_4 d_4 \times 3 \qquad \text{Eq. (15)}$$

The area $S_8$ of the gaps between the photoradiators 92 within the triangle $P_4$ is obtained as:

$$S_8 = S_6 + S_7 = \frac{1}{2} (d_4^2 \cos 30° + 3 r_4 d_4) \qquad \text{Eq. (16)}$$

Supposing that each photoradiator 92 is $H_4$ long, the volume $W_4$ of the culture medium filling the gaps between the photoradiators 92 is expressed as:

$$W_4 = S_8 H_4 = \frac{1}{2} (d_4^2 \cos 30° + 3 r_4 d_4) H_4 \qquad \text{Eq. (17)}$$

The area $S'''$ over which the light emitting surfaces of the photoradiators 92 contact the culture medium is provided as:

$$S''' = 3 r_4 H_4 \qquad \text{Eq. (18)}$$

The values $S'''$, $W_4$ and $S'''/W_4$ obtained with respect to various values of the distance $d_4$ between the photoradiators 92 and length of one side $r_4$ (radius) of each photoradiator are shown in Table 4.

TABLE 4

| cm $d_4$ | cm $r_4$ | cm $H_4$ | cm$^2$ $S'''$ | cm$^3$ $W_4$ | m$^2$/l $S'''/W_4$ |
|---|---|---|---|---|---|
| 0.05 | 0.5 | 30 | 45 | 1.157 | 3.889 |

TABLE 4-continued

| cm $d_4$ | cm $r_4$ | cm $H_4$ | cm² $S'''$ | cm³ $W_4$ | m²/l $S'''/W_4$ |
|---|---|---|---|---|---|
|  | 1.0 | 30 | 90 | 2.282 | 3.944 |
|  | 2.0 | 30 | 180 | 4.532 | 3.972 |
|  | 3.0 | 30 | 270 | 6.782 | 3.981 |
| 0.1 | 0.5 | 30 | 45 | 2.380 | 1.891 |
|  | 1.0 | 30 | 90 | 4.630 | 1.944 |
|  | 2.0 | 30 | 180 | 9.130 | 1.972 |
|  | 3.0 | 30 | 270 | 13.630 | 1.981 |
| 0.15 | 0.5 | 30 | 45 | 3.667 | 1.227 |
|  | 1.0 | 30 | 90 | 7.042 | 1.278 |
|  | 2.0 | 30 | 180 | 13.793 | 1.305 |
|  | 3.0 | 30 | 270 | 20.532 | 1.315 |
| 0.18 | 0.5 | 30 | 45 | 4.473 | 1.006 |
|  | 1.0 | 30 | 90 | 8.520 | 1.050 |
|  | 2.0 | 30 | 180 | 16.62 | 1.083 |
|  | 3.0 | 30 | 270 | 24.72 | 1.092 |
| 0.2 | 0.5 | 30 | 45 | 5.020 | 0.896 |
|  | 1.0 | 30 | 90 | 9.520 | 0.945 |
|  | 2.0 | 30 | 180 | 18.520 | 0.972 |
|  | 3.0 | 30 | 270 | 27.520 | 0.981 |

It will be seen from Table 4 that the ratio $S'''/W_4$ the condition $m^2/l \geqq 1$ as long as the distance $d_4$ between the adjacent photoradiators 92 is not more than 0.18 cm, and that the ratio $S'''/W_4$ is substantially dependent upon the distance $d_4$ and hardly affected by the radius ($r_3$) of the photoradiators 92. For the hexagonal photoradiators 92, the reaction bath may have a hexagonal or circular cross-section.

Figure 11:
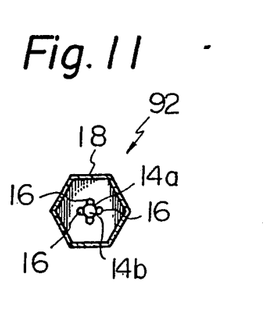
FIG. 11 is a section along line XI—XI of FIG. 10.
Figure 12:
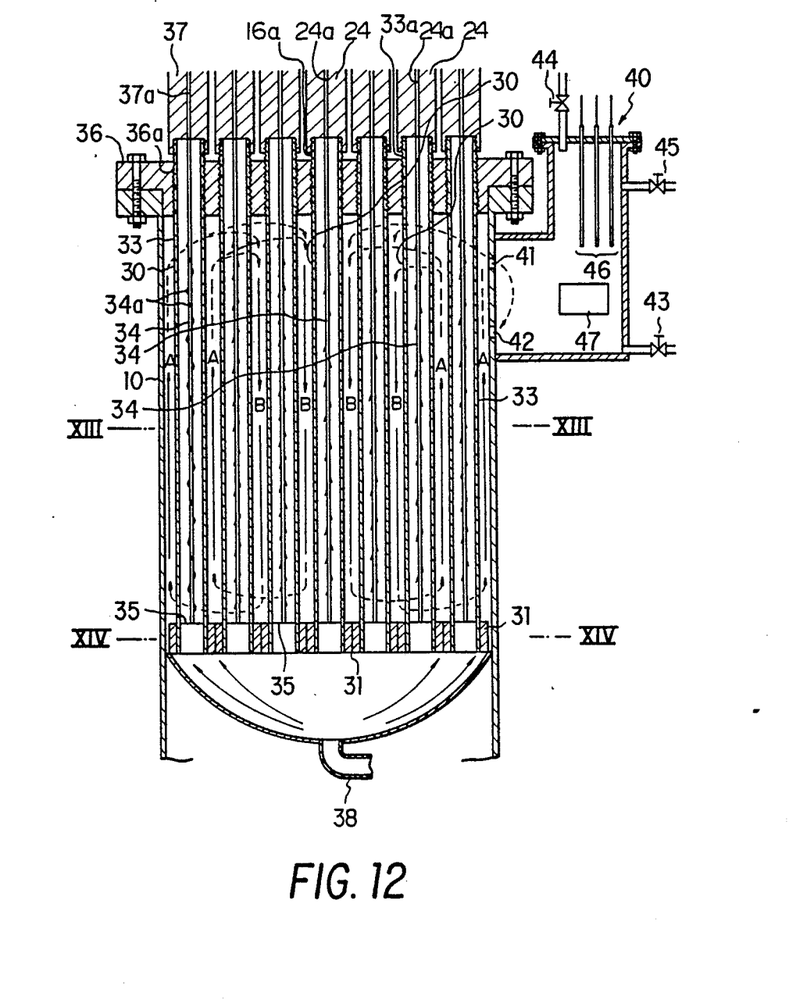
FIG. 12 is a sectional side elevation of an apparatus for photosynthesis according to another embodiment of the present invention.

FIGS. 11 and 12 illustrate an example of the photoradiators 92 suitable for emitting natural light in connection with the embodiment shown in FIG. 9. In these drawings, the same elements as those shown in FIG. 2 are designated by like reference numerals.

Figure 13:
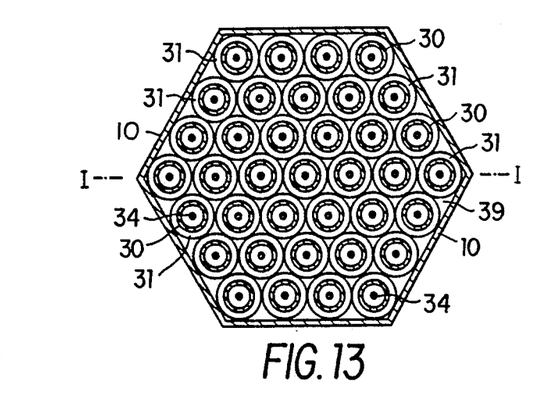
FIG. 13 is a section along line XIII—XIII of FIG. 12.
Figure 14:
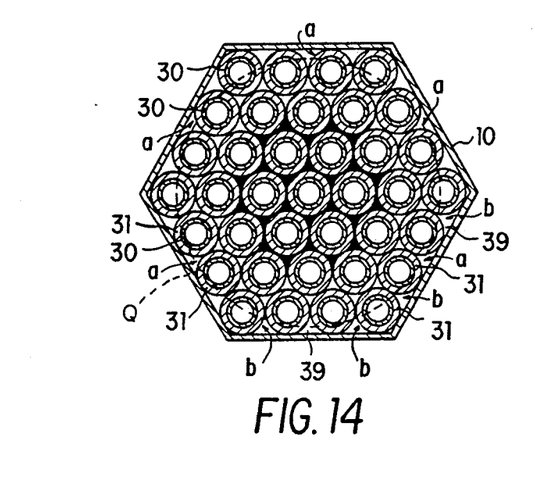
FIG. 14 is a section along line XIV—XIV of FIG. 12.

Referring to FIGS. 12-14 of the drawings, the photosynthetic apparatus includes a bath means or reaction bath which is generally designated by the reference numeral 10. A number of photoradiators 30 in the form of narrow tubes are arranged upright and in parallel with each other within the reaction bath 10. Each of the photoradiators 30 is rigidly fit in a short tube 31 at its lower end in a fluid tight manner. The photoradiator 30 comprises a transparent tube or sheath 33, an optical rod 34 and a mirror 35 located at a lower end portion of each photoradiator 30. A lid 36 removably covers the top of the reaction bath 10 and has threaded openings 36a in which threaded upper portions 33a of the respective tubes 33 are engaged. Thus, when the lid 36 is removed from the reaction bath 10, it is accompanied by the photoradiators 30 to facilitate cleaning of the reaction bath 10 or the photoradiators 30. Fiber optic cables 37 are in threaded engagement respectvely with the upper ends of the threaded portions 33a of the tubes 33 at their light output ends. In this position of each cable 37, its optical fiber 37a is aligned at its end with the end of the optical rod 34 in the associated photoradiator 30, so that the light propagating through the optical fiber 37a is effectively transferred to the optical rod 34.

Each optical rod 34 is made of quartz, plastics or the like. The rod 34 carries thereon a light diffusing material 34a at desiredly spaced locations along its length. The light diffusing material 34a has a refractive index which is larger than that of quartz or plastics, thereby causing the light to break through the material 34a out of the rod 34.

A conduit 38 is communicated with the reaction bath 10 to supply $CO_2$-containing air thereinto. As shown in FIG. 14, the short tubes 31 in which the lower ends of the photoradiators 30 are fit are bonded together at their outer surfaces while defining gaps 39 therebetween. In the illustrated embodiment, the gaps 39 are stopped up by plug members in a central area of the reaction bath 10 (black gaps 39 is FIG. 14). $CO_2$-containing air fed into the reaction bath 10 by the conduit 38 flows through the open gaps 39 adjacent to the periphery of the bath 10, advances upward through the spaces between the photoradiators 30 as indicated by arrow A in FIG. 12, flows toward the center of the bath 10 at the upper end of the latter, flows down along the center as indicated by arrows B, and is then redirected by the closed gaps 39 in the central area toward the periphery of the reaction bath 10, thus circulating within the reaction bath 10. With this arrangement, the circulating air moves at a substantial velocity along the outer periphery of each photoradiator 30 while entraining the culture medium, thereby preventing the photosynthetic substance from becoming deposited on the photoradiators 30. This frees the output light of the photoradiators 30 from interception to thereby supply all the photosynthetic substance with optical energy and $CO_2$ each in an even distribution.

It will be seen in the above embodiment that, if the area is made smaller at the region where the air flows downward than at the region where the air flows upward, the velocity of water will be increased at the downward flow region to minimize contamination to the photoradiators 30 in this region. While the gaps 39 in the central area of the bath 10 are stopped up in the illustrated embodiment, those in the peripheral area may be stopped up instead.

An auxiliary bath 40 is mounted on an upper side portion of the reaction bath 10 and communicated with the latter through openings 41 and 42 which are located one above the other A valve 43 is positioned in the vicinity of the lower end of the auxiliary bath 40 so as to discharge the product of photosynthesis from the apparatus. A second valve 44 is mounted on the top of the auxiliary bath 40. This valve 44 is operable to supplement the culture medium and pH control solution to make up for the shortage which results from the discharge of the product through the valve 43. A third valve 45 is mounted on an upper side portion of the auxiliary bath 40 in order to controllably let the air out of the reaction bath 10 to control the pressure inside the reaction bath 10. Where use is made of a pressure regulating valve as the valve 45 for automatically controlling the bath pressure to a reference level, the $CO_2$ concentration in the water can be increased to promote photosynthesis and, at the same time, the pressure in the reaction bath 10 is prevented from lowering to change $CO_2$ into $M^IHCO_3$. Disposed inside the auxiliary bath 40 are various instruments 46 for monitoring the photosynthetic reaction in the reaction bath 10, e.q. thermometer, pressure gauge, pH meter and densitometer. The conditions inside the reaction bath 10 are so controlled as to effect photosynthesis in an optimum manner in response to outputs of such instruments For example, the temperature in the reaction bath 10 may be controlled by controlling a heat generating/absorbing device 47 which is positioned in the auxiliary bath 40. Also, the outputs of the instruments are processed to notify the timing to collect the product.

As long as the photosynthetic reaction is to be carried out without interruption, the product will be collected through the auxiliary bath 40 . When interruption of the reaction is permissible, the end (not shown) of the conduit 38 may be communicated to a vacuum source (not shown) or the like instead of the $CO_2$-containing air supply, so that the product can be collected through the conduit 38.

Figure 15:
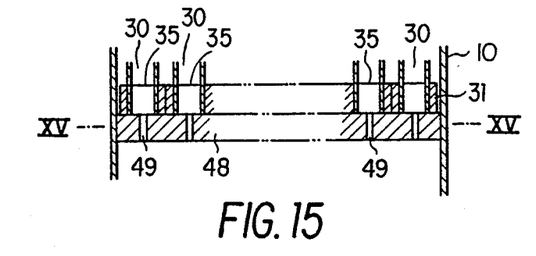
FIG. 15 is a fragmentary sectional side elevation of another embodiment of the present invention.
Figure 16:
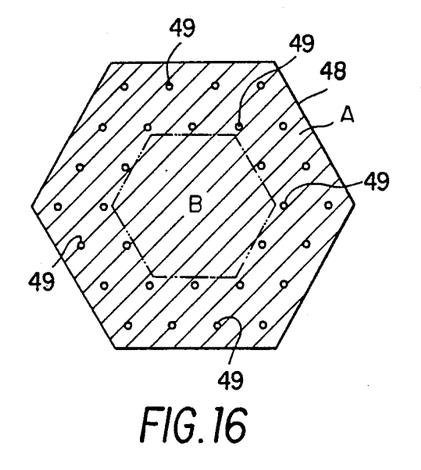
FIG. 16 is a section along line XV—XV of FIG. 15.

Referring to FIGS. 15 and 16, another embodiment of the present invention is shown which makes it needless to stop up the selected gaps 39 between the adjacent photoradiators 30. As previously described, the lower ends of the photoradiators 30 are respectively fit fluid-tight in the short tubes 31. The reference numeral 48 designates a baffle plate or obstruction plate which is rigidly supported by the reaction bath 10 in intimate contact with the bottoms of the photoradiators 30. The baffle plate 48 is formed with apertures 39 in its predetermined region A (corresponding to the region in FIG. 14 which does not contain the stopped-up gaps 39) and in positions corresponding to the gaps 39. The remaining region B of the baffle plate 48 is not formed with such apertures. In operation, the $CO_2$-containing air coming in through the conduit 38 is passed through the apertures 49 in the baffle plate 48 and caused to circulate in the reaction bath 10 in the manner described with reference to FIGS. 12–14. Thus, the baffle plate 48 eliminates the necessity of the operation for plugging the selected gaps 39 in the desired area, thereby cutting down the production cost of the apparatus.

Figure 17:
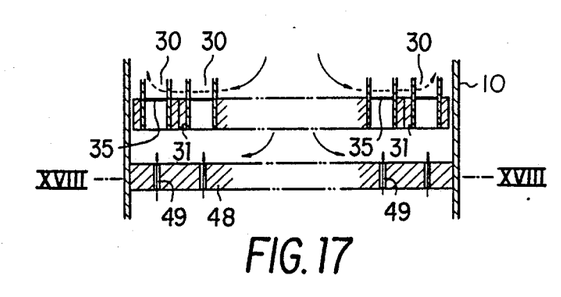
FIG. 17 is a view similar to FIG. 15 but showing another embodiment of the present invention.
Figure 18:
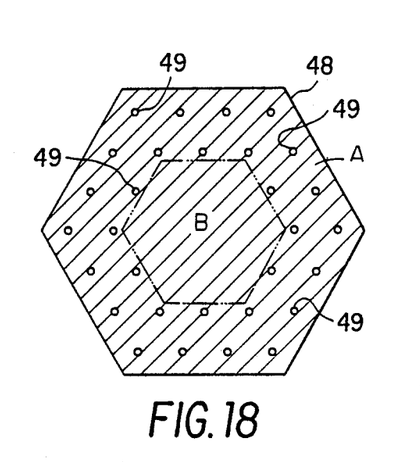
FIG. 18 is a section along line XVIII—XVIII of FIG. 17.
Figures 19, 20, 21:
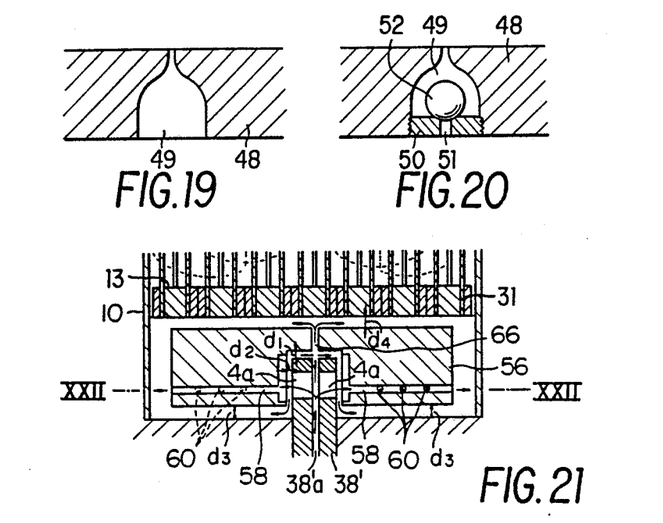
FIGS. 19 and 20 are sectional side elevations showing different examples of a check valve mechanism applicable to the present invention.
FIG. 21 is a fragmentary sectional side elevation of still another embodiment of the present invention.

Referring to FIGS. 17 and 18 another embodiment of the present invention is shown which is essentially similar to the embodiment of FIGS. 15 and 16 but different therefrom in the position of the apertured baffle plate 48. As shown, the baffle plate 48 formed with the apertures 49 are supported by the reaction bath 10 at a predetermined spacing from the lower ends of the photoradiators 30. The apertures 49 are formed through the baffle plate 48 in the same region A as in the embodiment shown in FIGS. 15 and 16. In this construction, the air supply through the conduit 38 causes part of the downwardly flowing culture medium to circulate radially outward through the gaps between the photoradiators 30. However, the rest of the culture medium is allowed to flow straight onto the baffle plate 48 and then circulate radially outward through the clearance between the bottoms of the photoradiators 30 and the baffle plate 48. This reduces the contamination to the upper end portions of the short tubes 31. Where the baffle plate 48 is spaced apart from the bottoms of the photoradiators 30 as in the embodiment shown in FIGS. 17 and 18, the photoradiators 30 may be arranged in intimate contact with each other without using the short tubes 31, in order to substantially eliminate the contamination to the outer walls of the photoradiators 30. In this case, it is necessary to make the diameter of each photoradiator 30 smaller at the upper end than the lower end so that a passage is defined for the culture medium flow upward along the periphery (or the center) of the reaction bath 10 to be circulated toward the center (or the periphery)

Where the baffle plate 48 is employed in the position shown in FIGS. 15 and 16 or in the position shown in FIGS. 17 and 18 the diameter of the apertures 49 may be determined to allow the culture medium to pass therethrough so that the product can be collected through the conduit 38 (FIG. 13) by the vacuum source or the like (not shown). Alternatively, the apertures 49 may be provided with a diameter which passes air therethrough but not the culture medium. FIGS. 19 and 21 illustrate other possible implements for allowing the air to pass through the apertures 49 into the reaction zone, while checking the culture medium in the reaction zone. In FIG. 19, each aperture 49 is generally tapered toward the reaction zone. In FIG. 20, a valve seat member 50 having a passageway 51 is threaded into each aperture 49 which is tapered as in the configuration of FIG. 19. The valve seat 50 coacts with a ball 52 movably received in the aperture 49. In any case, the aperture 49 furnished with such a checking function prevents the conduit 38 from being stopped up by the culture medium or the like.

Figure 22:
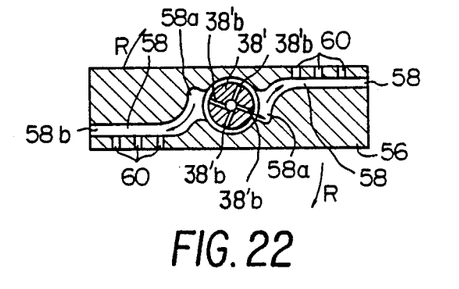
FIG. 22 is a section along line XXII—XXII of FIG. 21.

Referring to FIGS. 21 and 22, a further embodiment of the present invention is shown which is designed to achieve more efficient and positive recirculation of the culture medium within the reaction bath 10. In this embodiment, the conduit 38 (FIG. 12) has an extension 38' which protrudes into the reaction bath 10 to a position below the photoradiators 30. The conduit extension 38' is shaped at its upper end portion to have an axial passageway 38'a and a plurality of radial passageways 38'b which extend obliquely and radially outwardly from the axial passageway 38'a. A rotor 56 is movably coupled over the top of the conduit extension 38'. The rotor 56 is formed with passageways 58 and a plurality of air ejection ports 60 which extend throughout the rotor 56 from each of the passageway 58 as illustrated.

In operation, air fed through the axial passageway 38'a of the conduit extension 38' is discharged from the radial passageways 38'a to impinge on side wall portions 58a of the respective passageways 58, thereby giving the rotor 56 the tendency to rotate clockwise as indicated by arrows R in FIG. 22. The air passed through the passageways 58 are ejected from the ejection ports 60 to drive the rotor 56 in the direction R. The rotor 56 is caused to float by the air coming out through the upper end of the axial passageway 38'a of the conduit extension 38', a clearance $d_1$ thus developing between the upper end of the conduit extension 38' and the rotor 56. This part of the air, therefore, flows radially outward through the clearance $d_1$ as indicated by arrows in FIG. 21. Meanwhile, the air flowing through the gap $d_1$ and the air discharged from the radial passageways 38'b is partly routed through an annular clearance $d_2$ between the outer surface of the conduit extenson 38' and the inner wall of the rotor 56 into a clearance $d_3$ between the bottom of the rotor 56 and the bottom of the reaction bath 10. As a result, the air streams in the clearances $d_1$ and $d_3$ serve as an air cushion for supporting the rotor 56 while the air stream in the clearance $d_2$ functions as an air bearing for rotatably supporting the rotor 56. The major torque acting on the rotor 56 is created by the air jets from the ejection ports 60. If desired, the rotor 56 may be formed with a through upward passageway 62 to pass the air into a clearance $d_4$ between the bottoms of the photoradiators 30 and the top of the rotor 56. The air stream in this clearance $d_4$ will more effectively aircushion the rotor 56 in cooperation with the other air streams.

The embodiment described above with reference to FIGS. 21 and 22 achieves various advantages. Because the rotation of the rotor 56 affects the pneumatic pressure distribution in the bottom section of the reaction bath 10, the air circulation path in the reaction bath 10 progressively changes moment by moment. This as a whole distributes $CO_2$-containing air uniformly to all the air stream paths and, thereby, causes the reaction to occur more effectively. The culture medium, photosynthetic substance and the like falling toward the bottom of the reaction bath 10 are entrained upwardly by the air jets from the ejection ports 60, whereby dead part of the photosynthetic substance or the like is prevented from accumulating in the bottom of the reaction bath 10. If any such undesired accumulation is anticipated, the ejection ports 60 may be directed somewhat downwardly so that the accumulation will be scattered upwardly by the air jets. The bottom of the reaction bath 10 can thus be maintained clean for a long time. While the rotor 56 has been shown and described as being rotatably supported by the air bearing and air cushioning, use may be made of an ordinary mechanical bearing for the same purpose. The air bearing is still advantageous over the mechanical bearing because the rotor 56 needs only be placed between the conduit 38 and the photoradiators 30 and, therefore, it can be readily mounted and demounted to facilitate services.

Where the reaction bath 10 is formed not circular but polygonal such as hexagonal as in the foregoing embodiments, the passageways 58 formed in the rotor 56 may be extended to eject the air radially outward from the ends 58b of the rotor 56 and thereby effectively direct the air to the gaps 39 adjacent to the periphery of the reaction bath 10. Supposing that the outermost ends of the rotor 56 move along the locus indicated by a dotted circle Q in FIG. 14, the resistance to the air ejection is larger when the ports 58b are in the positions a close to the wall of the reaction bath 10 than when they are in the positions b remote from the bath wall. The air, therefore, can be supplied substantially evenly to the air passages in both sections a and b. The rotor 56 may be formed with air ejection ports which are directed upwardly toward the photoradiators 30, thereby forcibly causing the air to flow through the gaps 28 in accordance with the movement of the rotor 56. Furthermore, the forced circulation of air makes it needless to plug the selected gaps 39 (see FIG. 14).

In summary, it will be seen that the present invention provides a photosynthetic apparatus which can be effectively operated and readily scaled up due to the effective arrangement of photoradiators. Furthermore, the apparatus of the invention does not use any light source which contains a heat source such as a fluorescent lamp, thereby precluding the need for a measure against heat generation.

The present invention also provides an apparatus for photosynthesis which promotes efficient photosynthetic reaction despite its simple and compact construction. Also, the apparatus can be kept clean over a long period of time to facilitate maintenance and inspection.

Various modifications will become possible for those skilled in the art after receiving the teachings of the present disclosure without departing from the scope thereof. For example, each photoradiator 30 may have a structure whose refractive index is larger in a peripheral section than in a central section, omitting the light diffusing material 30a shown in FIG. 12. In this connection, the use of rod-shaped optical conductors 34 as in FIG. 12 ensures linearity and facilitates their installation in the photoradiators 30. Two or more optical fibers 37a may be accommodated in each fiber optic cable 37; at least one of the optical fibers may be supplied with converged sunlight and at least one of the rest with artificial light. This allows the natural and artificial light to be used selectively: only the sunlight when it is intense, both the sunlight and artificial light in the morning and evening as well as in cloudy weather, and only the artificial light when the sunlight is unavailable at all as in the night. The cross-section of the tubes 33 of the photoradiators 30 is not limited to the illustrated circle but may be a polygon such as a triangle, a square or a hexagon. Likewise, the hexagonal cross-section of the reaction bath 10 is not restrictive but may be replaced with any other desired one.

Various modifications will become possible for those skilled in the art after receiving the teachings of the present disclosure without departing from the scope thereof.

What I claim is:

1. Apparatus for photosynthesis comprising bath means containing a photosynthetic reaction bath, a plurality of tubular photoradiatiors arranged upright in said bath means in parallel array, said tubular radiators comprising a transparent tubular sheath and a quartz or plastic optical rod extending through said tubular sheath, upper support means and lower support means in said bath means for supporting the upper and lower end positions respectively of said tubular photoradiators, said tubular photoradiators being spaced from one another so as to define a plurality of upright passages between said tubular photoradiators, said upper support means closing off the upper ends of said upright passages, said bath means having a lower chamber underlying said lower support means, said lower support means having a flow-through portion which provides communication between said chamber and a first plurality of upright passages and a stopped-up portion which blocks communication between said chamber and a second plurality of upright passages, conduit means leading to said chamber for supplying $CO_2$-containing air, said flow-through portion and said stopped-up portion of said lower support means being constructed and arranged such that said air passes from said chamber through said flow-through portion into said first plurality of upright passages, said air passing upwardly in said first plurality of upright passages and subsequently being directed generally laterally by said upper support means such that the air then passes downwardly in said second plurality of upright passages to subsequently again be directed generally laterally by said stopped-up portion of said lower support means to once again pass upwardly in said first plurality of upright passages, whereby the air circulates in said bath means between said tubular photoradiators.

2. Apparatus for photosynthesis comprising bath means containing a photosyntetic reaction bath, a plurality of polygonal photoradiators arranged upright in said bath means in parallel array, upper support means and lower support means in said bath means for supporting the upper and lower end portions respectively of said polygonal photoradiators, said polygonal photoradiators being spaced from one another so as to define a plurality of upright passages between said polygonal photoradiators, said upper support means closing off the upper ends of said upright passages, said bath means having a lower chamber underlying said lower support means, said lower support means having a flow-through portion which provides communication between said chamber and a first plurality of upright passages and a stopped-up portion which blocks communication between said chamber and a second plurality of upright passages, conduit means leading to said chamber for supplying $CO_2$-containing air, said flow-through portion and said stopped-up portion of said lower support means being constructed and arranged such that said air passes from said chamber through said flow-through portion into said first plurality of upright passages, said air passing upwardly in said first plurality of upright passages and subsequently being directed generally laterally by said upper support means such that the air then passes downwardly in said second plurality of upright passages to subsequently again be directed generally laterally by said stopped-up portion of said lower support means to once again pass upwardly in said first plurality of upright passages, whereby the air circulates in said bath means between said polygonal photoradiators.

3. Apparatus according to claim 2, wherein said polygonal photoradiators have a cross-sectional configuration selected from the group consisting of a triangle, a square and a hexagon.

* * * * *